United States Patent [19]

Ranganathan et al.

[11] Patent Number: 5,527,926
[45] Date of Patent: Jun. 18, 1996

[54] METHODS AND COMPOSITIONS FOR USING NON-IONIC CONTRAST AGENTS TO REDUCE THE RISK OF CLOT FORMATION IN DIAGNOSTIC PROCEDURES

[75] Inventors: Ramachandran S. Ranganathan, Princeton; Radhakrishna K. Pillai, Kendall Park, both of N.J.

[73] Assignee: Bracco International B.V., Amsterdam, Netherlands

[21] Appl. No.: 473,561

[22] Filed: Jun. 6, 1995

Related U.S. Application Data

[60] Division of Ser. No. 893,865, Jun. 5, 1992, which is a continuation-in-part of Ser. No. 708,656, May 31, 1991, abandoned, which is a continuation-in-part of Ser. No. 617,716, Nov. 26, 1990, abandoned.

[51] Int. Cl.⁶ .................. C07D 307/14; C07D 207/09; C07D 333/22; A61K 49/04
[52] U.S. Cl. .................. 549/480; 548/543; 548/550; 548/952; 546/243; 549/68; 549/424; 549/28; 549/410; 549/88; 549/346; 549/9; 540/485; 540/527; 424/9.44
[58] Field of Search .................. 549/480, 68, 424, 549/28, 88, 410, 9, 346; 424/9.44; 546/243; 548/550, 543, 952; 540/485

[56] References Cited

U.S. PATENT DOCUMENTS

| | | | |
|---|---|---|---|
| 2,658,904 | 11/1953 | Galler | 549/72 |
| 2,750,393 | 6/1956 | Elpern | 424/9.44 |
| 2,776,241 | 1/1957 | Priewe et al. | 564/153 |
| 3,306,927 | 2/1967 | Larsen | 564/153 |
| 3,701,771 | 10/1972 | Almen et al. | 564/153 |
| 3,883,535 | 5/1975 | Felder et al. | 424/9.44 |
| 3,925,412 | 12/1975 | Obendorf et al. | 424/9.44 |
| 3,975,534 | 8/1976 | Enders et al. | 548/543 |
| 4,001,298 | 1/1977 | Gries et al. | 564/153 |
| 4,066,743 | 1/1978 | Kneller | 424/9.44 |
| 4,066,743 | 1/1978 | Kneller | 424/9.44 |
| 4,250,113 | 2/1981 | Nordal et al. | 564/153 |
| 4,352,788 | 10/1982 | Felder et al. | 564/153 |
| 4,845,235 | 7/1989 | Matumoto et al. | 548/550 |
| 5,075,502 | 12/1991 | Kneller et al. | 424/9.44 |
| 5,278,311 | 1/1994 | Arunachalam et al. | 546/243 |
| 5,359,077 | 10/1994 | Ranganathan et al. | 546/219 |
| 5,384,107 | 1/1995 | Singh et al. | 424/9 |

FOREIGN PATENT DOCUMENTS

| | | |
|---|---|---|
| 0390242 | 10/1990 | European Pat. Off. |
| 319226 | 12/1974 | Norway |

OTHER PUBLICATIONS

Fumagalli, et al., "Radiopaque Contrast Media", *Pharmazie*, 30, H.2, pp. 78–79, 1974.

Stormorken et al., "Effect of Various Contrast Media on Coagulation, Fibrinolysis, and Platelet Function; An In Vitro and In Vivo Study", *Investigative Radiology*, vol. 21, Apr. 1986, pp. 348–354.

Mamon et al., "Biochemical Evidence for a Relative Lack of Inhibition of Thrombin Formation by Nonionic Contrast Media", *Radiology*, 1991; 179:399–401.

G. B. Hoey et al., "Chemistry of X–Ray Contrast Media" pp. 23–125, 1980.

Laerum et al., "Postphlebographic Thrombosis", *Diagnostic Radiology*, Sep. 1981, pp. 651–654.

*Primary Examiner*—Richard L. Raymond
*Assistant Examiner*—Deborah Lambkin
*Attorney, Agent, or Firm*—George P. Hoare, Jr.; Donald L. Rhoads

[57] ABSTRACT

In accordance with the present invention a novel method and composition for using nonionic contrast media to reduce the risk of clot formation in a diagnostic procedure is disclosed. Novel compositions for such method are also disclosed. The present method comprises employing a triiodinated phenyl contrast agent having a heterocyclic group or a dimeric triiodinated phenyl contrast agent having one or more heterocyclic groups.

6 Claims, No Drawings

METHODS AND COMPOSITIONS FOR USING NON-IONIC CONTRAST AGENTS TO REDUCE THE RISK OF CLOT FORMATION IN DIAGNOSTIC PROCEDURES

This is a divisional of application Ser. No. 07/893,865, filed Jun. 5, 1992, which is a continuation-in-part of 07/708,656, filed on May 31, 1991, now abandoned which is a continuation-in-part of 07/617,716, filed on Nov. 26, 1990, now abandoned.

BACKGROUND OF THE INVENTION

Non-ionic contrast media, e.g. iopamidol and iohexol, for use in angiography, have enjoyed wide-spread acceptance in the diagnostic field in recent years. The primary reasons for this revolve around the fact that the frequency of adverse reactions to intravenous injection of non-ionic contrast media, compared with most ionic contrast media (e.g., diatrizoate, sodium meglumine and the like) is reduced by a factor of two.

In a limited number of cases, however, clotting has been observed during administration of the angiographic procedure utilizing non-ionic agents. Investigations into this infrequent, but disturbing, phenomenon have unanimously confirmed that the contrast media themselves, whether ionic or non-ionic, are not actively thrombogenic. Several in vitro studies agree that the ionic contrast media typically have greater anticoagulant effects as compared to their non-ionic counterparts. Careful selection of any appropriate contrast medium for angiographic procedures therefore involves a consideration of, among other factors, the inherent lower chemotoxicity of the non-ionics balanced against the greater anticoagulant effects of the ionics.

Researchers now believe this rare clotting phenomenon to be the result of the procedure employed by the practitioner. Apparently, in cases where aspirated blood is allowed to stand in the contrast material syringe, i.e. in contact with the non-ionic agent, for several minutes prior to the procedure, thrombus formation is possible. Various modifications and improvements to technique are considered to be the primary solution to this limited problem. Nevertheless, another measure to safeguard against this potential technique-induced clotting has been the utilization of anticoagulant agents. This measure is also called for in subjects who are otherwise prone to thrombus formation.

One widely used agent known for its anticoagulant activity is heparin. It is generally believed that the angiographic procedure does not warrant systemic heparin administration, although systemic heparin administration has been used, especially in subjects with histories of hyper-aggregation. Combinations of heparin and the contrast media have been tried in these types of procedures. This has not been without difficulties, however. Considering the naturally competing processes of coagulation and fibrinolysis and the problems which an imbalance in either direction may cause, that is, thromboses or hemorrhage, respectively, it is generally understood that employment of heparin is not without risks. Further, it is believed that some cases of cardiac ischaemia and ischa.._.iic brain injury may be the result of heparinisation during angiography.

European Patent Application 0 390 242 teaches that the red blood cell aggregation in human blood can be reduced by the addition of sodium chloride to nonionic contrast medium at a concentration of 20–60 mM. This approach, however, has the undesirable effect of increasing the osmolality of the non-ionic contrast medium.

Improved compositions and methods for using non-ionic contrast media in either angiographic procedures or patients where enhanced potential for thrombus formation exists would be a useful addition to the art.

SUMMARY OF THE INVENTION

In accordance with the present invention a novel method and composition for using nonionic contrast media to reduce the risk of clot formation in a diagnostic procedure is disclosed. Novel compounds for such method are also disclosed. The present method comprises employing a triiodinated phenyl contrast agent having a heterocyclic group or a dimeric triiodinated phenyl contrast agent having one or more heterocyclic groups.

DETAILED DESCRIPTION OF THE INVENTION

The present invention pertains to methods and compositions using nonionic contrast media to reduce the risk of clot formation in circumstances where the potential for clot formation exists. As described above, such risks may be the result of the particular angiographic procedure or technique employed or may be inherent in the patient to be subjected to the diagnostic procedure. Our copending U.S. application Ser. No. 710,884 (and EP 431,838) entitled "NEW NON-IONIC RADIOGRAPHIC CONTRAST AGENTS" discloses that an unexpected degree of anticoagulant behavior was observed in the compound

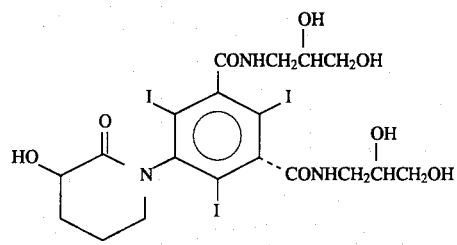

It has now been found that the class of triiodinated phenyl compounds having an unsubstituted or appropriately substituted heterocyclic group, or dimeric forms thereof having one or more heterocyclic groups, have properties indicating anticoagulant behavior greater than that of nonionic agents lacking such heterocyclic substitution. In some cases the anticoagulant activity is equal to or greater than that of ionic contrast agents. This is believed to provide an enhanced measure of safety for all diagnostic procedures, especially those wherein the potential for clot formation is thought to be a problem. Further, it is expected that dimeric forms containing a heterocyclic group will behave similarly. Thus, the present methods and compositions have the advantage of less side effects as compared to using ionic agents, but with anticoagulant properties greater than those of other non-ionic agents and anti-coagulant properties equal to or greater than those of the ionic agents.

The nonionic contrast agents having anticoagulant properties which are useful in the present methods and compositions include a triiodinated phenyl nucleus

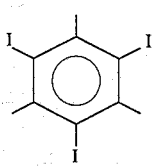

which has a heterocyclic substituent at one or more than one of the positions not substituted with iodine. Preferred are those compounds having 4–6 hydroxy groups and most preferred are those having 5 hydroxy groups. Especially preferred are those compounds having most of the hydroxy groups at positions remote to the heterocyclic group(s). For example, compounds having 1 or 2 hydroxy groups on the heterocyclic moiety and 3 or 4 of its hydroxy groups at $R_1$ and $R_2$ in formula I below, are believed to be more stable and less toxic.

The heterocyclic group or groups are preferably selected from

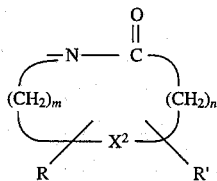 (A)

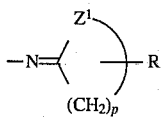 (B)

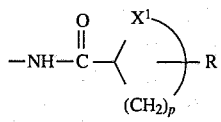 (C)

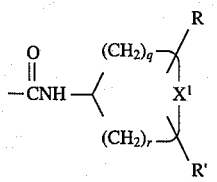 (D)

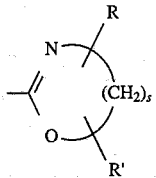 (E)

wherein R and R' are independently selected from hydrogen, alkyl, hydroxy, alkoxy, hydroxyalkyl and alkoxyalkyl;

$X^1$ is

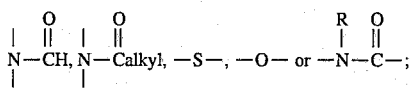

$X^2$ is $X_1$ or —$CH_2$—;
m is 1–4 or if $X^2$ is —$CH_2$—, m is 0–4;
n is 0–3;
p is 2–5;
q and r are independently 1 or 2; and
s is 2–5.

Preferably the triiodinated phenyl contrast agent is of the formula

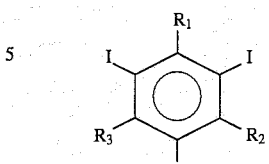 I wherein $R_1$ is

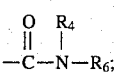

$R_2$ is

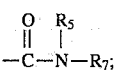

$R_3$ is heterocyclo;
$R_2$ can be —W—Z, where Z is

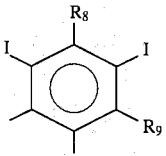

W is a linking group; and wherein
$R_8$ is

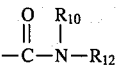

or heterocyclo;
$R_9$ is

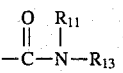

or heterocyclo;
$R_4$, $R_5$, $R_{10}$ and $R_{11}$ are the same or different and are hydrogen, alkyl or hydroxyalkyl;
$R_6$, $R_7$, $R_{12}$ and $R_{13}$ are the same or different and are hydrogen, alkyl or hydroxyalkyl;
W is —X—Y—X— wherein
X is $$-\underset{R_{14}}{N}-CO- \text{ or } -CO-\underset{R_{14}}{N}-;$$

Y is

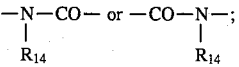

$R_{14}$ and $R_{14}'$ are independently H, alkyl or hydroxyalyl;
A is a single bond, —O—, —S— or —N—$COR_{14}$;
n is 0 to 6;
alkyl refers to single or branched carbon chains of 1 to 6 carbons and hydroxyalkyl refers to such groups having one or more hydroxy moieties. Preferred hydroxyalkyl groups include

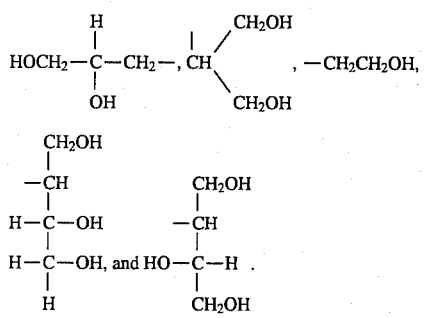

Examples of triiodinated phenyl compounds having heterocyclic groups from category (A) have been disclosed as nonionic contrast agents in our copending application filed concurrently herewith, incorporated herein by reference and entitled "NEW NONIONIC RADIOGRAPHIC CONTRAST AGENTS" (which is related to EP 431,838. That copending application discloses compounds of the formula

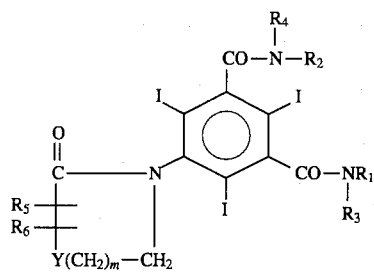

wherein Y is a single bond, —CH$_2$CH$_2$—, —CH$_2$O—, —OCH$_2$—,

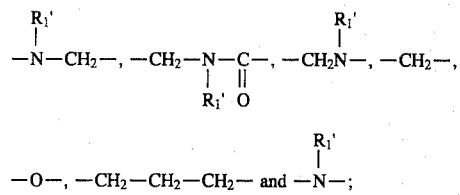

—O—, —CH$_2$—CH$_2$—CH$_2$— and —N(R$_1$')—;

R$_1$, R$_1$' and R$_2$ are the same or different and are hydrogen, alkyl or hydroxyalkyl, such as

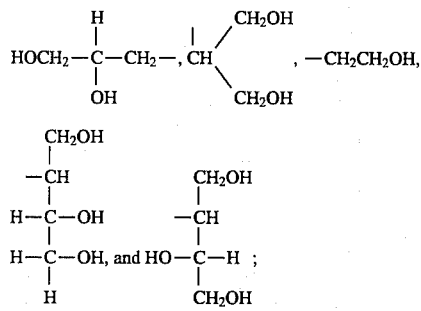

R$_3$ and R$_4$ are the same or different and are hydrogen, alkyl or hydroxyalkyl;

R$_5$ is hydrogen, alkyl, hydroxyalkyl, such as —CH$_2$CH$_2$OH, CH$_2$OH or OH; and R$_6$ is alkyl, hydroxyalkyl, such as —CH$_2$CH$_2$OH, CH$_2$OH or OH, or hydrogen and may be the same or different than R$_5$ and m is zero or one, with the proviso that no methylene or methine carbon atom of the heterocyclic ring is attached to both a nitrogen and an oxygen atom with the additional proviso that when Y is a single bond, m is not zero. The term alkyl refers to straight or branched chain groups of one to six carbon atoms including methyl, ethyl and propyl.

The preparation of compounds of our copending application wherein the heterocyclic group (A) is oxazolidinyl with 4-hydroxymethyl substitution is illustrated by the following scheme:

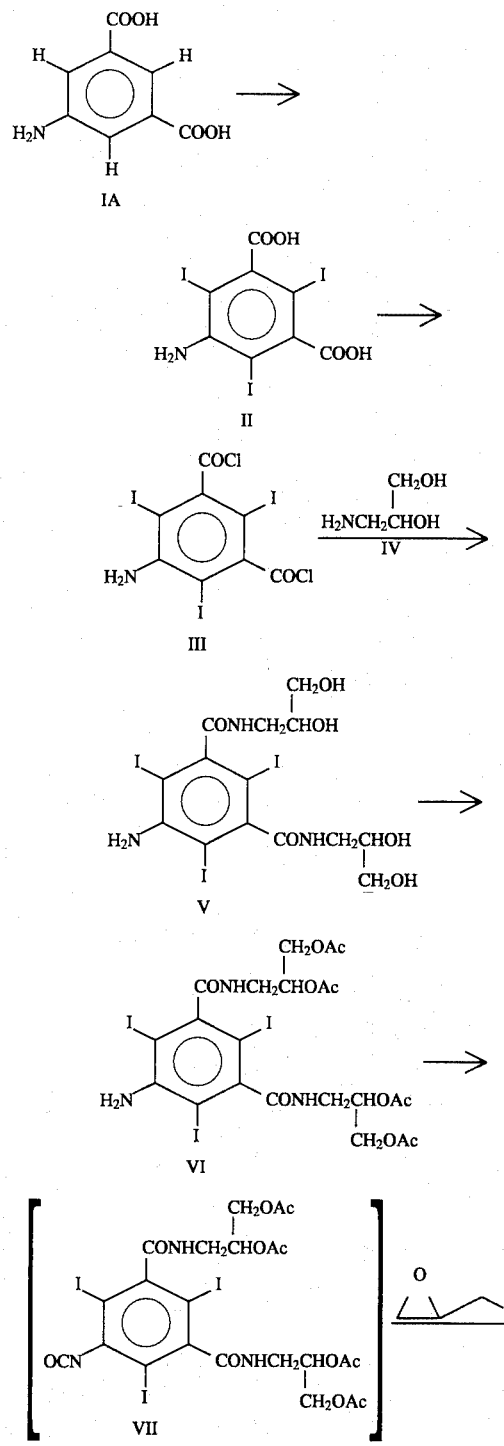

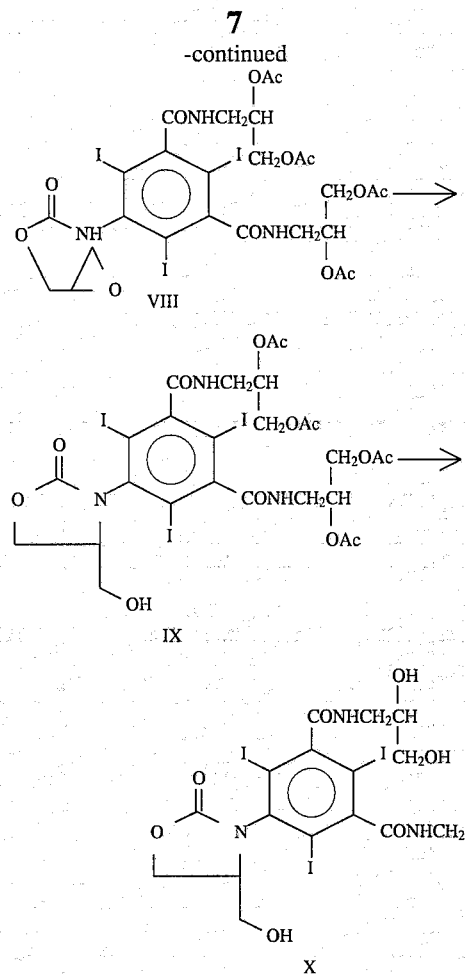

Compound IA which is commercially available is iodinated with a compound such as potassium iododichloride in dilute hydrochloric acid solution to obtain 5-amino-2,4,6-triiodo-1,3-benzenedicarboxylic acid (II). Compound II is chlorinated with purified thionyl chloride to obtain the corresponding bis-chloride (III). Compound III is then amidated with 1-amino-2,3-propanediol (IV) to obtain the isophthalamide V. Compound V is then selectively O-acylated with acetic anhydride in pyridine to yield 5-amino-N,N'-bis [2,3-bis(acetyloxy)propyl]2,4,6-triiodo-1,3-benzene-dicarboxamide (VI). Aminodehalogenation of compound VI by treatment with a toluene solution of phosgene in ethyl acetate at 60° over a period of sixteen hours results in a conversion into the corresponding isocyanate (VII). When the reaction is over, the solvents along with unreacted excess phosgene and hydrogen chloride, that was liberated during the course of the reaction, are removed by distillation. Any trace of acid left behind, is removed by repeated co-distillations with ethyl acetate.

Addition of glycidol to the crude isocyanate (VII), in the presence of catalysts such as cuprous chloride or phenylmercuric acetate, in ethyl acetate at room temperature overnight yields oxiranylmethyl [3,5-bis[[[2,3-bis(acetyloxy)propyl]amino]carbonyl-2,4,6-triiodophenyl]carbamate (VIII).

A basic solution of the glycidyl carbamate (VIII) is heated at 75° for 30 minutes. Intramolecular cyclization occurs to afford N,N'-bis[2,3-bis(acetyloxy)propyl]-5-[4-hydroxymethyl)-2-oxo-3-oxazolidinyl]-2,4,6-triiodo-1,3-benzene-dicarboxamide (IX), as the sole product, after crystallization from aqueous methanol.

Deacetylation of the tetraacetate (IX) by treatment with sodium methoxide in methanol, followed by neutralization with Dowex-50($H^+$) resin and decolorization with charcoal, yields N,N'-bis(2,3-dihydroxypropyl)-5-[4-(hydroxymethyl)-2-oxo-3-oxazolidinyl]-2,4,6-triiodo-1,3-benzenedicarboxamide (X). This product is desalted and further purified by low pressure reverse phase column chromatography. Crystallization from water or from aqueous isopropanol yields compound X.

Substituted pyrrolidin-2-one derivatives with no substitution at the 5 position of the heterocycle are prepared according to the following scheme:

The amide of formula XI, which is formed using the methodology described in the previous scheme, is reacted with an ω-halo-acid halide to obtain the anilide of compound XII followed by cyclization of compound XII to the pyrrolidine-2-one of formula XIII.

The compounds of our copending application wherein the heterocyclic group is a piperidin-2-one and $R_5$ and $R_6$ are each hydrogen can be prepared by reacting compound XI with an appropriately substituted bromopentanoyl bromide of the formula in a suitable solvent such as dimethylacetamide to yield the corresponding anilide of the formula

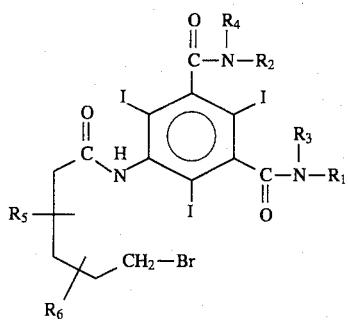

XV which upon treatment with a base such as potassium carbonate in a suitable solvent such as dimethyl-acetamide will yield the desired piperidin-2-one of the formula

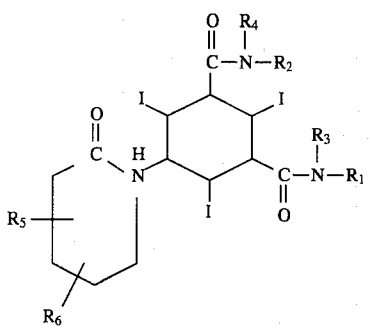

XVI

When $R_5$ or $R_6$ is hydroxyl or hydroxymethyl in compound XVI it is protected as the corresponding acetate or ether which is eventually deprotected by conventional means. A halogen substituent on the piperidine-2-one ring can be converted into an acetyloxy group by treatment with silver acetate in acetic acid or with tetraethylammonium acetate in a suitable solvent. Solvolysis of the acetate with aqueous methanolic sodium hydroxide or methanol in the presence of sodium methoxide will give compound XVI wherein $R_5$ and/or $R_6$ is hydroxy or $CH_2OH$. To obtain such substituted derivatives, for example, the dibromo-anilide

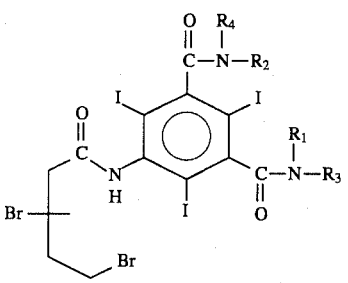

XVII can be ring closed to the 3-bromo-piperidin-2-one

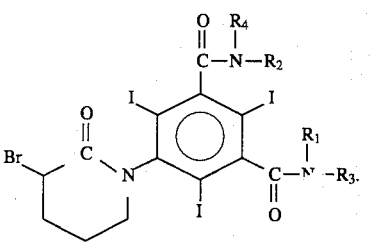

XVIII

The bromo moiety of compound XVIII can be converted into the acetate and then to the corresponding hydroxy compound by the methods described above.

2,5,Dibromopentanoyl bromide used in the preparation of compound XVII is prepared by treating δ-valerolactone with bromine in the presence of red phosphorous. 2,5,Dibromopentanoyl bromide is condensed with compound XI to form compound XVII.

Triiodinated phenyl derivatives of formula I having heterocyclic group (B) attached thereto are novel compounds shown by the formula

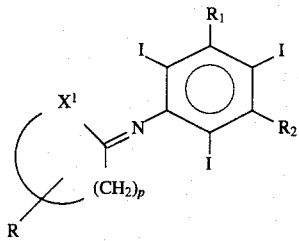

XIX wherein R is selected from hydrogen, alkyl, hydroxy, alkoxy, hydroxyalkyl and alkoxyalkyl;

$X_1$ is

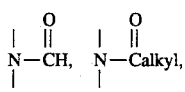

—S— or —O—;

p is 2–5;

$R_1$ is

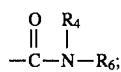

$R_2$ is

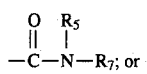

$R_2$ can also be —W—Z, where Z is

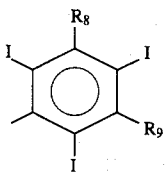

W is a linking group;
and wherein
$R_8$ is

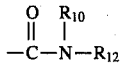

or heterocyclo;
$R_9$ is

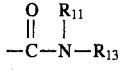

or heterocyclo;

$R_4$, $R_5$, $R_{10}$ and $R_{11}$ are the same or different and are hydrogen, methyl or —$CH_2CH_2OH$;

$R_6$, $R_7$, $R_{12}$ and $R_{13}$ are the same or different

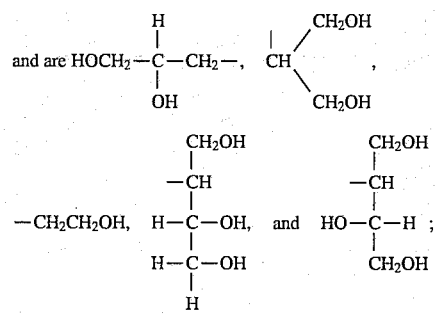

and
W is —X—Y—X— wherein
X is

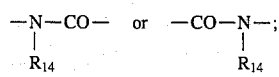

Y is

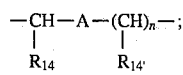

$R_{14}$ and $R_{14}'$ are independently H, alkyl or hydroxyalkyl;
A is a single bond, —O—, —S— or —N—$COR_{14}$;
n is 0 to 6.

In the definitions throughout this present application, the term "alkyl" refers to branched or straight chain carbon groups of 1–6 atoms, and hydroxyalkyl refers to such groups having one or more hydroxy moieties. Preferred hydroxyalkyl groups are those in the definitions of $R_6$, $R_7$, $R_{12}$ and $R_{13}$ above.

Preferred novel compounds of formula XIX are those wherein
$X^1$ is oxygen;
p is 3;
R is hydroxyalkyl;
$R_4$ and $R_5$ are each hydrogen; and
$R_6$ and $R_7$ are each hydroxyalkyl.

Most preferred of the novel compounds of the present invention wherein

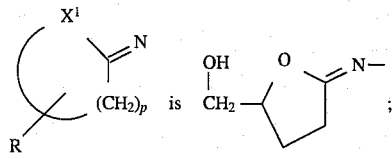

is
$R_4$ and $R_5$ are each hydrogen; and,
$R_6$ and $R_7$ are each

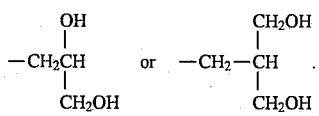

To prepare the novel compounds of the present invention, a compound of formula XI is treated with 4-pentenoyl chloride,

XX $CH_2=CHCH_2CH_2COCl$ in an aprotic solvent, e.g., dimethylacetamide, to provide the corresponding pentenoyl anilide

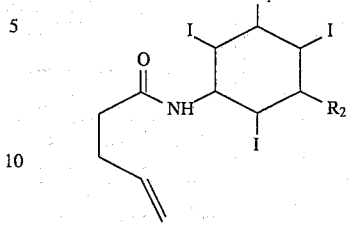

XXI where $R_1$ and $R_2$ are understood to be protected when they contain active functionalities, e.g., —OH, —SH and NHR groups. Final products in protected form can be deprotected using known methodology.

The 4-pentenoyl chloride XX was prepared from 4-pentenoic acid using known procedures. (Ascher, "Constitution of Isanic and Isanolic Acids, Ann.", 589, 222–38, 1954; Chem. Abs., 50, 1599.)

Compound XXI can thereafter be treated with N-iodosuccinimide in a solvent, e.g., chloroform, to provide

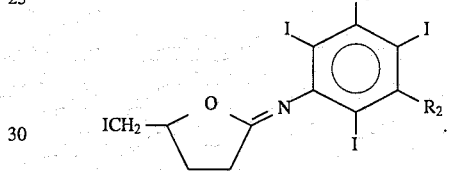

XXII

Compound XXII is then subjected to acetyloxylation, e.g., by treatment with silver acetate in acetic acid to provide compounds of the formula

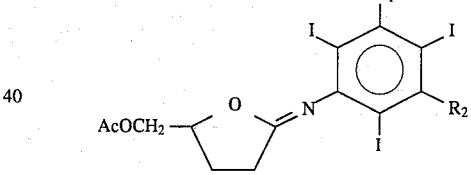

XXIII

Deacetylation, such as by treatment with sodium methoxide in methanol, provides the desired product

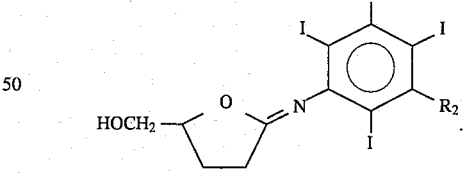

XIVa

Compounds of formula XI can also be reacted with a compound of the formula

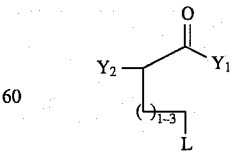

(where $Y_1$ and $Y_2$ are independently H or OH, L is a leaving group, e.g., Cl or Br)
in the presence of preferably a base or a Lewis acid catalyst to provide compounds of the formula

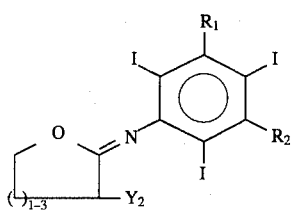

Most preferably the Lewis acid catalyst is AlCl$_3$ or SnCl$_4$.

Examples of triiodinated phenyl compounds having the heterocyclic group

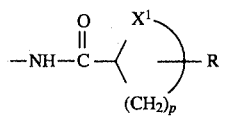

are known and have been disclosed for example by G. B. Hoey et al. in *The Chemistry of X-Ray Contrast Media*, Chapter 1, Radiocontrast Agents, Mr. Sovak (Ed.) Springer-Verlag, Berlin, 1984, incorporated herein by reference. A well-described example of this class is the compound Iogulamide (MP-10013)

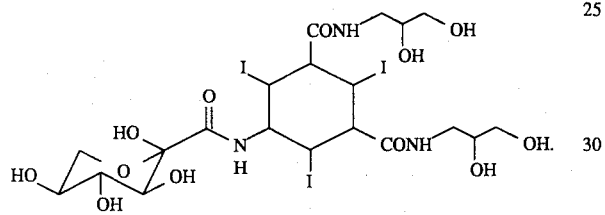

Novel examples of triiodinated phenyl compounds having the heterocyclic group (C) are disclosed in our copending application, filed concurrently herewith, incorporated herein by reference and entitled "NONIONIC RADIOGRAPHIC CONTRAST AGENTS". These compounds have the general formula

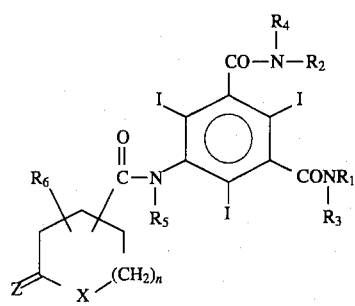

wherein X is selected from —O—, —S—,

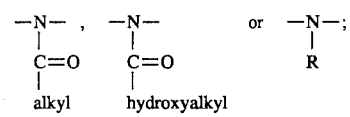

Z is H,H, alkyl or hydroxyalkyl when X is other than

or Z is O when X is

R is hydrogen, alkyl or hydroxyalkyl;

R$_1$ and R$_2$ are independently selected from H, alkyl, hydroxyalkyl;

R$_3$, R$_4$ and R$_5$ are independently selected from hydrogen, alkyl, or hydroxyalkyl; R$_6$ is alkyl, O-alkyl, CH$_2$O-alkyl, —CH$_2$CH$_2$OH, CH$_2$OH, OH, hydrogen or I; and n=0 or 1; where alkyl and hydroxyalkyl are as defined above for the novel compounds of class B.

Such compounds are prepared using Schemes (1)–(11) below.

Scheme 1

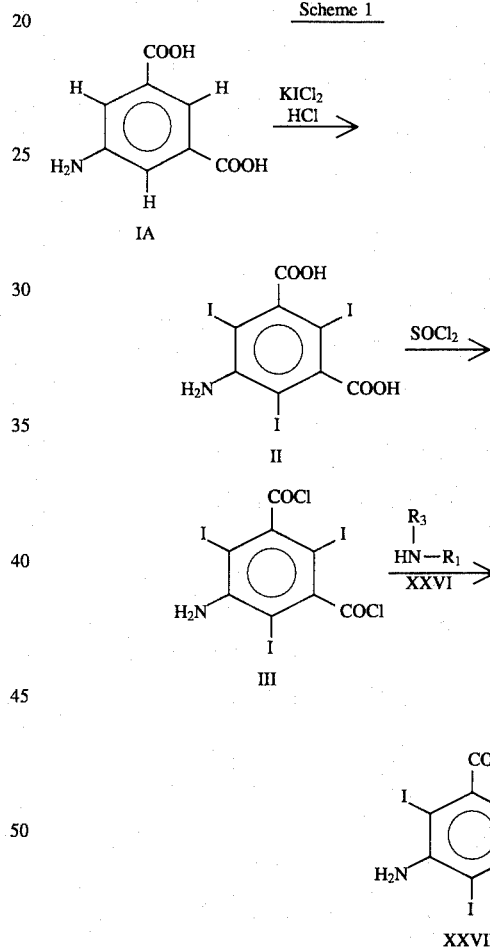

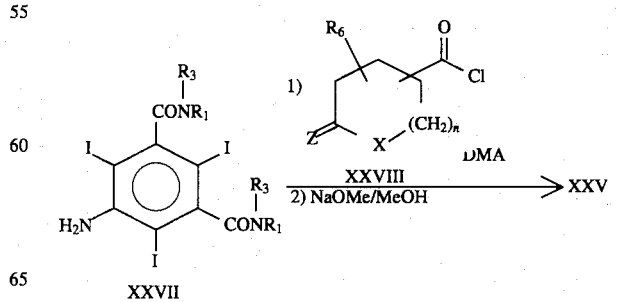

Scheme 2
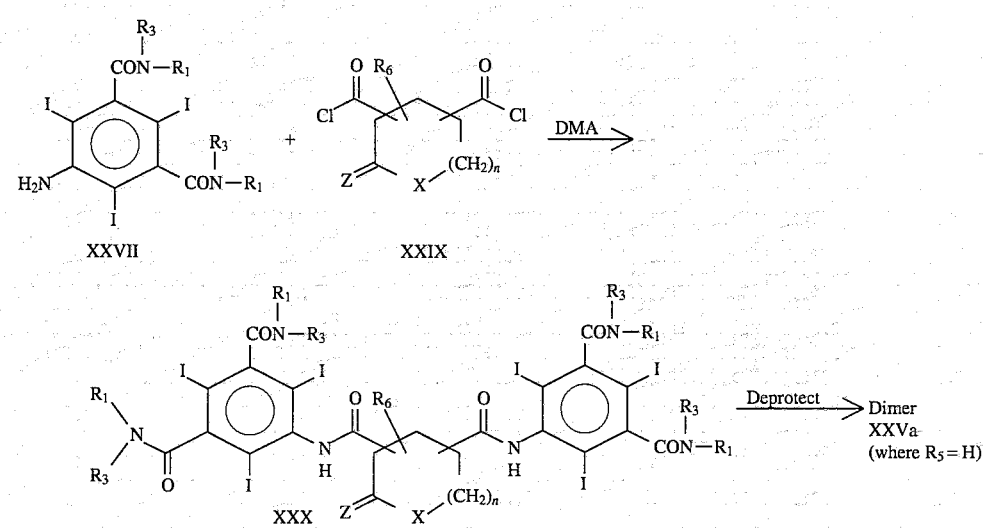
Scheme 3
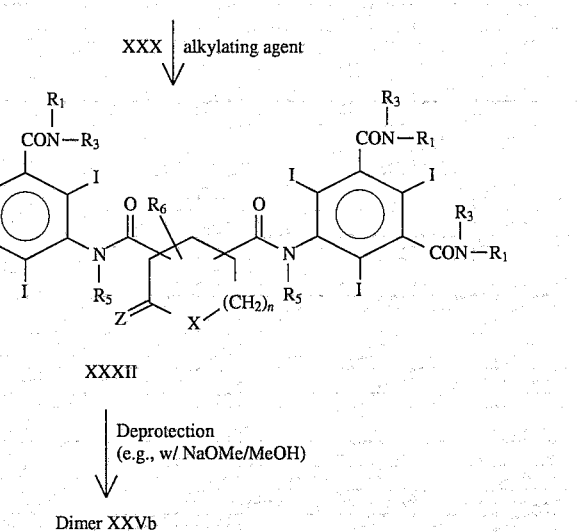
Scheme 4
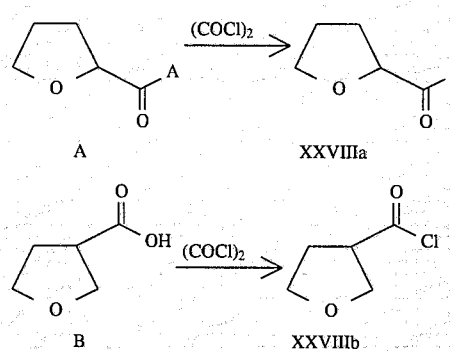
Scheme 5
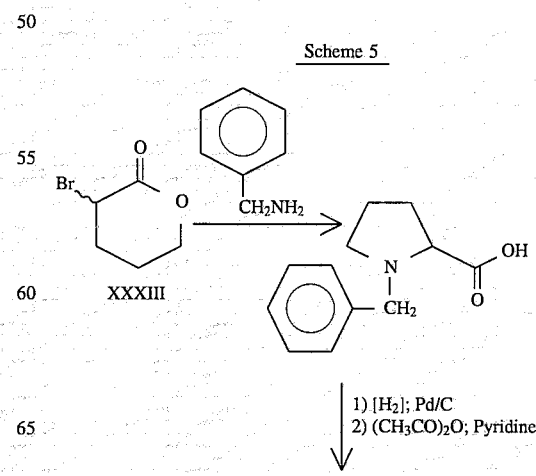

-continued
Scheme 5
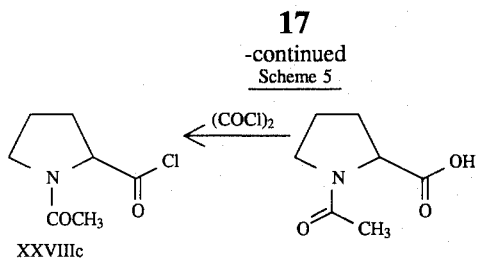
Scheme 6
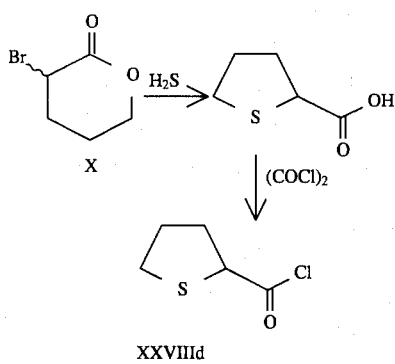
Scheme 7
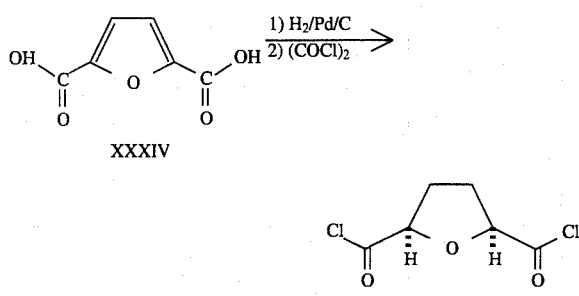
Scheme 8
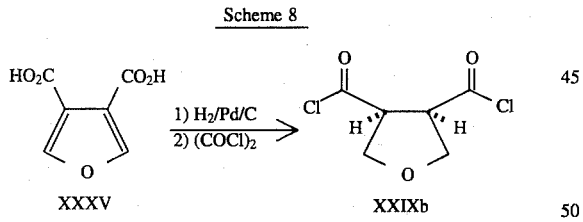
Scheme 9
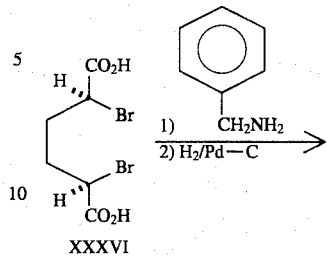
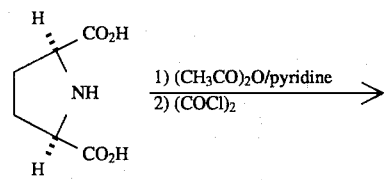
Scheme 10
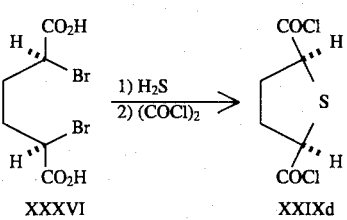

Scheme 11

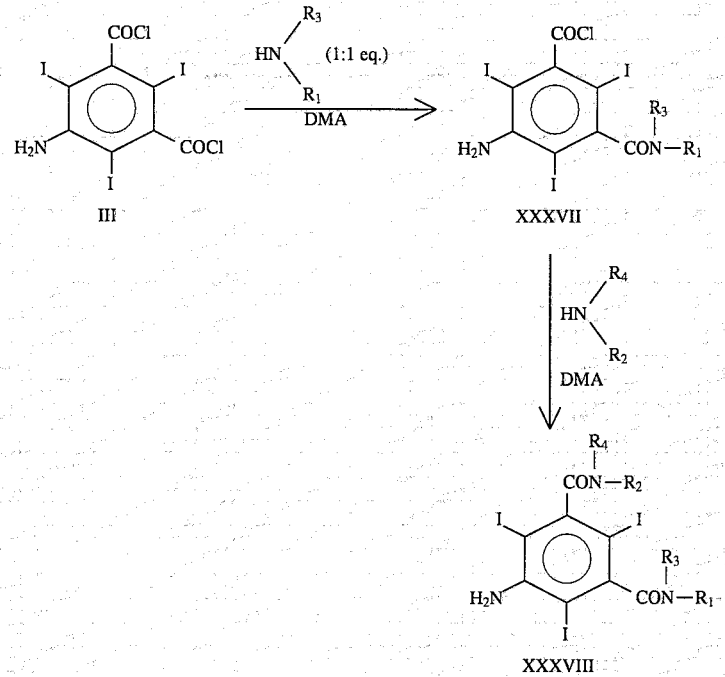

The compounds of the present invention, wherein

is the same as

can be prepared according to Scheme 1.

Compound IA which is commercially available is iodinated with a compound such as potassium iododichloride in dilute hydrochloric acid solution to obtain 5-amino-2,4,6,-triiodo-1,3-benzenedi-carboxylic acid (II). Compound II is chlorinated with purified thionyl chloride to obtain the corresponding bis-chloride (III). Compound III is then amidated with the desired intermediate of formula XXVI to obtain the isophthalamide XXVII. The hydroxy groups in any of $R_1$–$R_4$ in compound XXVII are protected, for example, by selective O-acylating (e.g. treatment with acetic anhydride in pyridine). Thereafter, compound XXVII is reacted with the carbonyl chloride XXVIII in an activating solvent, such as N,N-dimethylacetamide and then deacetylated, to provide the products of formula XXV. Removal of acetate protecting groups can be carried out by known techniques, such as by treatment with NaOMe and methanol.

The dimer XXVb is prepared analogously, as shown in Scheme 2, by reacting compound XXVII with a bifunctional bis-carbonyl chloride XXIX to obtain the protected dimers XXX. Removal of acetate protecting groups can be carried out as above to obtain the dimer XXVa where $R_5$=H.

Alternatively, the protected dimer can be alkylated by treatment with alkylating agents, as shown in Scheme 3, such as methyl iodide, 2-bromoethanol, 3-chloropropane-1,2-diol and the like, to obtain the bis-N-alkylated product XXXII wherein $R_5$ is methyl, hydroxyethyl, or 2,3-dihydroxypropyl etc. Removal of the acetate protecting groups affords the N,N'-bis-alkylated dimer XXVb, wherein $R_5$ is other than H.

The compound of formula XXVIII, wherein X=O and n=zero, is made by treating commercially available tetrahydro-2-furoic acid or tetrahydro-3-furoic acid with oxalyl chloride to obtain the corresponding acid chlorides XXVIIIa or XXVIIIb, as shown in Scheme 4. The compounds of formula XXVIII, wherein X=NHCOCH$_3$ and n=zero, XXVIIIc are made from commercially available α-bromo-δ-valero-lactone XXXIII as shown in Scheme 5. The compound of formula XXVIII wherein X=S and n=zero, is made from α-bromo-δ-valero-lactone XXXIII as shown in Scheme 6. The higher homologs wherein n>1 is made by analogous methods. The compound of formula XXIX, wherein X=O, n=zero and the COCl functions are at carbon atoms 2 and 5, is made from commercially available furan-2,5-dicarboxylic acid (XXXIV) as shown in Scheme 7. In a similar manner starting from furan-3,4-dicarboxylic acid (XXXV), the compound of formula XXIX wherein X=O, n=zero, and the COCl functions are at carbon atoms 3 and 6, is prepared as shown in Scheme 8.

The compound of formula XXIX wherein X=NHCOCH$_3$, n=zero and the COCl functions are at carbon atoms 2 and 5, is made from commercially available meso-2,5-dibromoadipic acid (XXXVI) as shown in Scheme 9. Similarly, by reacting meso-2,5-dibromoadipic acid (XXXVI) with H$_2$S, the S analog of structure XXIX, wherein X=S, n=zero, and the COCl functions at carbon atoms 2 and 5 is made as shown in Scheme 10.

Compounds of formula I where

does not equal

can be prepared as shown in Scheme 11. The bis-chloride III is treated in DMA with 1:1 equivalent of the first amine $HNR_1R_3$ in DMA under mild conditions, preferably between 0°–20° to obtain the mono-amide XXXVII, which is then treated with the second amine $HNR_2R_4$ in DMA to provide the unsymmetrical bis-amide XXXVIII. The unsymmetrical bis-amide XXXVIII is then processed as described for the symmetrical bis-amide XXVII to obtain the corresponding desired compounds XXV, XXVa and XXVb.

Compounds of formula XXVIII where X is NR and Z is O can be readily prepared by treating 2-pyrrolidine-5-carboxylic acid with $SOCl_2$ and $(COCl)_2$. Compounds of formula XXIX where X is NR and Z is O can be prepared by treating 2-pyrrolidine-5-carboxylic acid as described by F. Effenberger et al., *J. Org. Chem.* 55, 3064 (1990) to provide the diacid which can thereafter be converted to the bis-acid chloride XXIX by treatment with $SOCl_2$ or $(COCl)_2$.

Examples of triiodinated phenyl compounds having the heterocyclic group

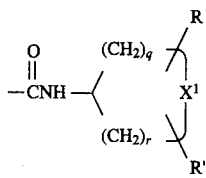

can be found in U.S. Pat. No. 4,021,481 which discloses compounds of the general formula

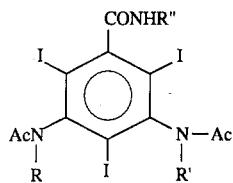

wherein R and R' are H, alkyl, or hydroxyalkyl;
R" is alkyl, poly- or mono-hydroxyalkyl. A well known example of this class of compounds is metrizamide.

Examples of compounds having the heterocyclic group

are also known and have been disclosed in U.S. Pat. No. 4,066,743 to Kneller. The '743 patent specifically discloses compounds (and preparation thereof) of the formula

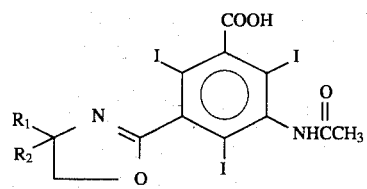

where $R_1$ is hydroxymethyl and $R_2$ is selected from hydroxymethyl or $C_{1-4}$alkyl.

The dimers, wherein the linking group does not have heterocyclic moieties, are made by methods well described in prior art. Well-known examples of dimers are Iotrolan and Ioxaglic acid.

The clotting index of an agent is a way of using the clotting time of that agent in plasma to indicate anticoagulant behavior. Thus, it is believed that agents having higher APTT indices, have greater anticoagulant activity. A perusal of Table 1 reveals that the acyclic nonionic contrast agents studied have APTT Index values in the range 0.2 to 0.3. On the other hand, Metrizamide which is a heterocycle substituted nonionic contrast agent belonging to the class D, as per our definition, has an APTT Index value of 0.8. All the novel heterocycle substituted NICM candidates disclosed in this patent, belonging to the classes A and B, have APTT Index values in the range 0.4–2.6. At least two of the new NICM have values greater than the ionic NICM, vig., Hexabrix and Renografin, which had values 0.9 and 1.0, respectively. Among the heterocycles, those bearing branched hydroxymethyl substituents have values in the lower range of 0.3 to 0.5. The hydroxy substituted congeners have values in the middle range of 0.6 to 0.8 and the unsubstituted analogs have the highest values in the range 2.0 to 2.6.

Structures for TABLES 1 and 2

Isovist-240 (Iotrolan)

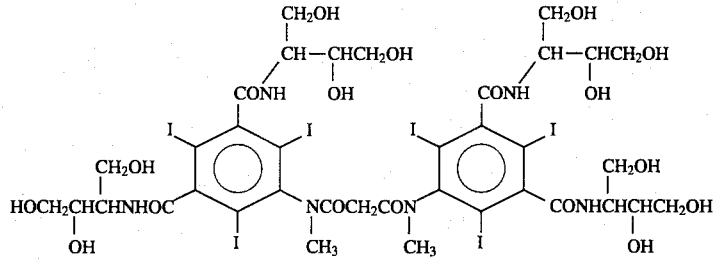

Optiray-320 (Ioversol)

-continued
Structures for TABLES 1 and 2
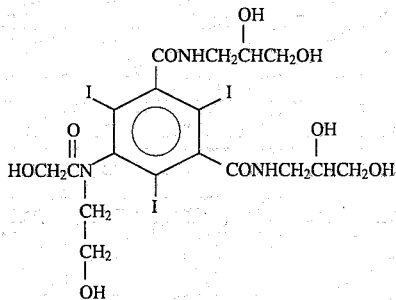
Omnipaque 350 (Iohexol)
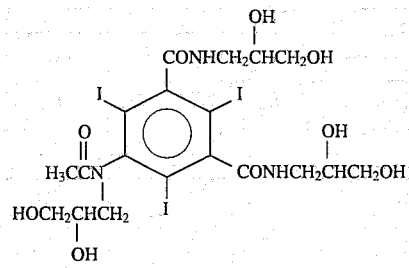
Isovue-370 (Iopamidol)
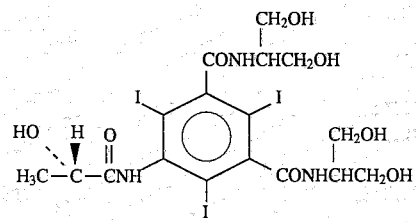
Ultravist-370 (Iopromide)
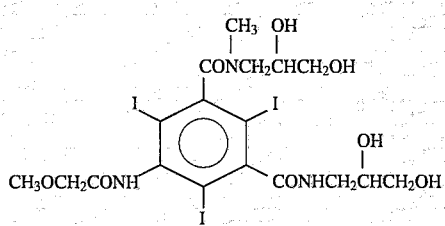
3 HM5-Iomorphol-A
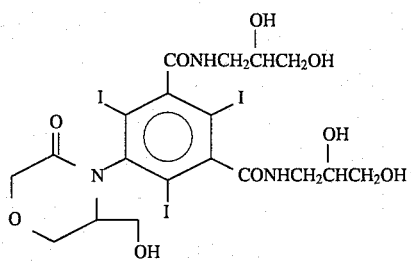
2 HM5-Iopyrol-A -continued
Structures for TABLES 1 and 2
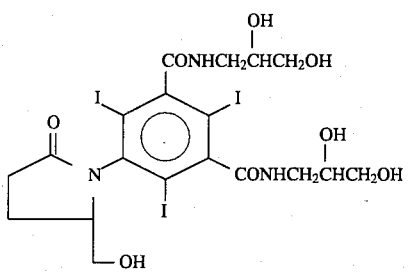
5 HM-Iofurol-A
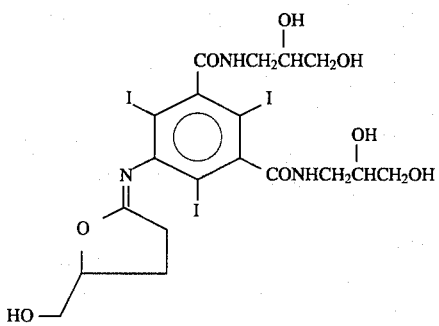
3 H2-Iopyrol-A
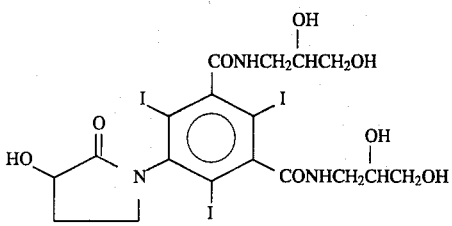
3 H2-Iopyrol-S
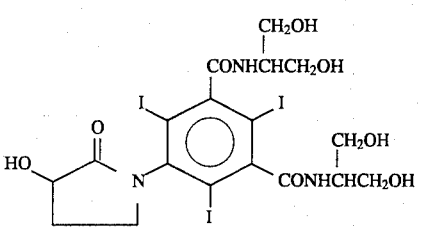
3 H2-Iopiperidol-A
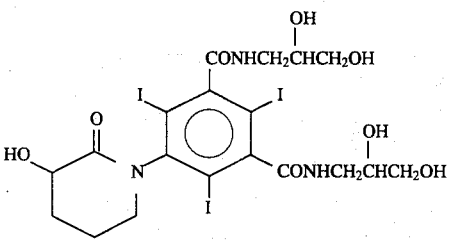
Metrizamide -continued
Structures for TABLES 1 and 2
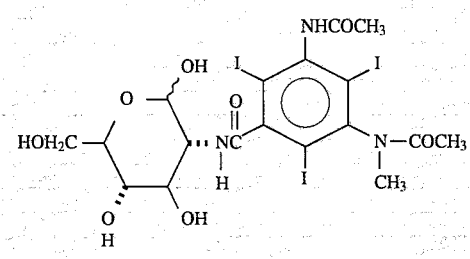
Hexabrix-320 (Ioxaglic Acid/Ioxaglate Sodium/
Ioxaglate meglumine)
Ioxaglic Acid
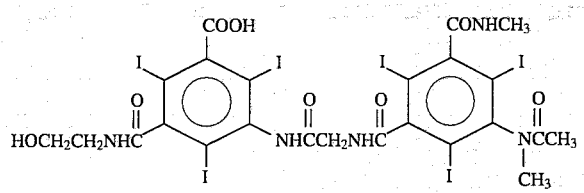
in combination with the sodium and meglumine salts
thereof.
Renografin-76 (Diatrozoate Meglumine)
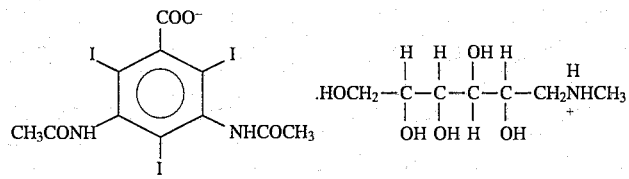
2-Iopyrol-A
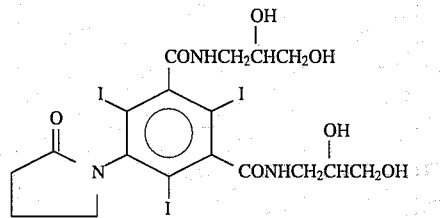
2-Iopiperidol-A
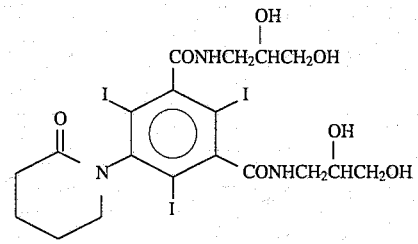
2-Iofuranol-A
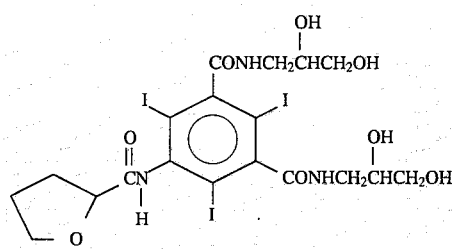

-continued
Structures for TABLES 1 and 2

3.3 DM Iozetidol-A

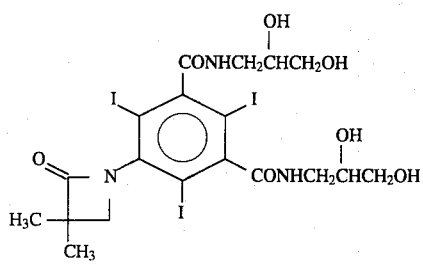

3 H2-Iozepinol-A

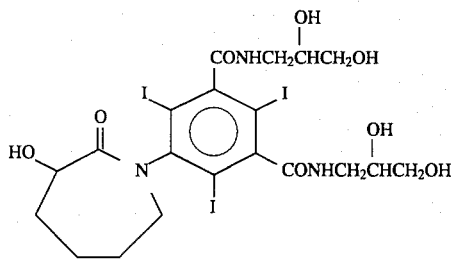

3 H2-Iopiperidol-BP

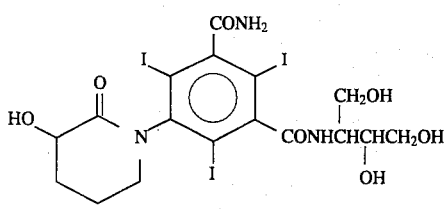

TABLE 1

APTT Index for Contrast Agents and the New NICM Candidates[1]

| Compound Name | Clotting Index (I)[2] |
|---|---|
| 0.9% Saline | — |
| Isovist-240 | 0.2 |
| Optiray-320 | 0.3 |
| Ominpaque-350 | 0.3 |
| Isovue-370 | 0.3 |
| Ultravist-370 | 0.3 |
| 3HM5Iomorphol-A | 0.4 |
| 2HM5-Iopyrol-A | 0.4 |
| 5HM-Iofurol-A | 0.5 |
| 3H2-Iopyrol-A | 0.6 |
| 3H2-Iopyrol-S | 0.6 |
| 3H2-Iopiperidol-A | 0.8 |
| Metrizamide | 0.8 |
| Hexabrix-320[3] | 0.9 |
| Renografin-76[3] | 1.0 |
| 2-Iopyrol-A | 2.0 |
| 2-Iopiperidol-A | 2.6 |

[1] All measurements were carried out at a concentration of 370 mg I/mL, unless otherwise stated.
[2] $I = (T_c - T_s) / (T_r - T_s)$, where $T_c$ is the clotting time for the substance, $T_s$ is the clotting time for 0.9% saline, and $T_r$ is the clotting time for Renografin-76.
[3] Ionic NICM.

TABLE 2

DED-Style APTT

| | Clotting Time (sec) | Clotting Index |
|---|---|---|
| Saline | 30.1 | — |
| Renografin | 69.6 | 1.00 |
| 2-Iofuranol-A | 42.2 | 0.31 |
| 3H2-Iopiperidol-A | 56.2 | 0.66 |
| 33 DM Iozetidol-A | 104.1 | 1.87 |
| 3H2-Iopiperidol-BP | 64.8 | 0.88 |
| Isovue 370 | 38.5 | 0.21 |
| 3H2-Iopiperidol-A | 52.5 | 0.57 |
| 3H2-Iozepinol-A | 70.4 | 1.02 |

The compounds, compositions and methods of the invention are suitable for use in most fields of application in which water soluble radiopaque compounds are necessary, such as vasography, urography, arthrography, and for the visualization of body cavities containing cerebrospinal fluid. When formulated with addition agents which increase the viscosity of the aqueous solutions, the present compounds may be employed to advantage for bronchography and hysterosalpingography.

The radio-opaque compounds of formula XIX of the invention can be employed as active ingredients of aqueous compositions for visualization of the cardiovascular system, e.g., coronary angiography, and for cerebral angiography. Because of their non-ionic nature, they are suited for visualization of body cavities containing spinocerebral liquor such as in radiculography, ventriculography and myelogrpahy.

Aqueous compositions for the applications indicated above may be formulated to contain a single novel heterocyclic-containing compound of the present invention or prior art compounds otherwise disclosed herein, or more than one compound, if the individual compounds are very pure.

The radio-opaque compositions of the invention are aqueous solutions containing 15 g and more of the compounds per 100 ml, eqivalent to 50 to approximately 500 mg iodine per ml. The more concentrated solutions are generally preferred, and they are applied in a manner generally known and selected according to the body cavity which it is intended to visualize. In vasography, the solutions are injected or infused into the vessels, particularly the blood vessels. Intravenous injection is resorted to in urography. For myelography and radiculography, the solutions are instilled after lumbar or suoccipital puncture. The amounts of solution necessary generally are 5 to 15 ml for myelography, 3 to 5 ml for radiculography, and 1 to 2 ml for ventriculography.

Solutions or suspensions of the novel contrast agents described herein may also be administered enterally. For suspended solutions 1–100 millimoles of a contrast agent suspended in 1–2 liters of physiological compatible carrier liquid is suitable.

The x-ray contrast compositions containing the novel compounds of the invention as active ingredients are prepared in a very simple manner since no salt-forming or solubilizing ingredients are needed. Any one of the novel compounds of the examples may be dissolved under sterile conditions in the desired amount of double-distilled water, and the solution so obtained is ready to be received in vials and sterilized. The compounds are not decomposed at sterilizing temperatures during the usual sterilizing periods (30 minutes at 120° C. or 60 minutes at 100° C.).

The new heterocycle based non-ionic contrast agents described herein have improved features not present in currently available contrast agents. Their superior stability characteristic, eliminates the need to use organic buffers or carbon dioxide saturation during sterilization of their formulations by autoclaving.

The new heterocycle based non-ionic contrast agents described herein are found to have excellent properties as to tolerance, stability, osmolality, viscosity and the like, factors important in angiography and urography.

Further, these novel heterocyclic non-ionic contrast agents of formula XIX, and all of the triiodinated phenyl compounds having heterocyclic groups (A), (B), (C), (D) or (E), including dimers thereof, are now believed to have anticoagulant properties equal to or greater than standard nonionic contrast agents such as iopamidol, iohexol or ioversol and some of the new heterocyclic agents also have anti-coagulant properties equal to or greater than ionic contrast agents such as diatrizonic acid or ioxaglic acid. Thus, the methods, compositions and novel agents herein provide reduced risk of clot formation in instances where clot formation is believed to be a problem.

The present application will be further illustrated by the following examples but should not be limited to the details described therein.

EXAMPLE 1

[N, N'-Bis(2,3-dihydroxypropyl]-5-[[dihydro-5-(hydroxymethyl) -2(3H)-furanylidene]amino]-2,4,6-triiodo-1, 3-benzenedicarboxamide A. N,N'-Bis(2,3-bis(acetyloxy)propyl]-2,4,6-triiodo -5-[(1-oxo-4-pentenoyl)amino]-1,3-benzenedicarboxamide 4-Pentenoyl chloride (7.44 g, 62 mmol) was added to a stirred solution of 5-amino-N,N'-bis-[2,3-bis(acetyloxy)propyl]-2,4,6-triiodo-1,3-benzene-dicarboxamide (21.8 g, 25 mmol) in dimethylacetamide (150 mL) at room temperature and the mixture was stirred for 16 hours. Dimethylacetamide was removed in vacuo and the residue dissolved in ethyl acetate (250 ml). The solution was washed with aqueous sodium bicarbonate (10%, 100 mL) and with water (2×100 mL). The organic layer was dried and the solvent removed to obtain the crude product as an off-white solid. Further purification by crystallization from a mixture of ethyl acetate (250 mL) and hexane (50 mL) afforded the title A compound (21.3 g), m.p. 225°–27°. TLC: Rf 0.50 in ethyl acetate. Mass Spectrum: m/z 956 (M+H)$^+$, 830, 653.

Elemental analysis calc'd for $C_{27}H_{32}I_3N_3O_{11}$: C, 33.95; H, 3.38; I, 39.85; N, 4.40; O, 18.42. Found: C, 33.94; H, 3.24; I, 39.68; N, 4.30.

B. N,N'-Bis[2,3-bis(acetyloxy)propyl]-5-[[dihydro -5-(iodomethyl)-2(3H)-furanylidene]amino]-2,4,6-triiodo-1, 3-benzenedi-carboxamide To a solution of the title A compound (14.3 g, 15 mmol) in chloroform (300 mL), N-iodosuccinimide (4.48 g, 2 mmol) was added and the mixture heated at 50° for 1 hour. The progress of this reaction was monitored both by TLC and by reverse phase HPLC. At the end of 1 hour the reaction was found to be complete. Chloroform was distilled off, the residue thus obtained dissolved in ethyl acetate (300 mL). The resulting solution was washed successively with water (100 mL), aqueous sodium thiosulfate (25%, 2×50 mL), and water (2×100 mL). The organic layer was dried and the solvent removed to obtain the product as a light yellow glassy solid (16.6 g). This crude product was further purified by column chromatography over silica gel (200 g, 45 cm column length) using ethyl acetate as eluent collecting 50 mL fractions. Fractions containing the pure product were combined and removal of the solvent afforded the title B compound as a glassy solid (13.0 g). TLC: R$_f$ 0.47 in ethyl acetate. Mass Spectrum: m/z (M+H)$^+$1082, 907, 781.

Elemental analysis calc'd for $C_{27}H_{31}I_4N_3O_{11}$: C, 30.19; H, 2.94; I, 46.57; N, 3.86; O, 16.44. Found: C, 30.15; H, 2.77; I, 46.25; N, 3.72.

C. 5-[[5-[(Acetyloxy)methyl]dihydro-2-(3H)-furanylidene]amino]-N,N'bis(acetyloxy)propyl]-2,4,6-triiodo-1,3-benzenedicarboxamide To a solution of the title B compound (16.32 g, 150 mmol) in glacial acetic acid (165 mL), was added silver acetate (10.01 g, 600 mmol), and the mixture stirred at 80° for 16 hours. The insoluble materials were filtered off, acetic acid removed in vacuo at 60°, the residue dissolved in ethyl acetate (200 mL), and the resulting solution washed successively with water (100 mL), aqueous sodium bicarbonate (200 mL) and water (100 mL). The ethyl acetate layer was dried and removal of the solvent afforded the crude product as a red colored solid. Purification by column chromatography over silica gel using a solvent gradient varying from 25% hexane in ethyl acetate to 10% hexane in ethyl acetate afforded pure title C compound as a light pink glassy solid (13.2 g). TLC: R$_f$ 0.35 in ethyl acetate. Mass Spectrum: m/z (M+H)$^+$1014, 888, 839, 713.

Elemental analysis calc'd for $C_{29}H_{34}I_3N_3O_{13}$: C, 34.37; H, 3.38; I, 37.57; N, 4.15; O, 20.53; Found: C, 34.37; H, 3.53; I, 37.88; N, 4.17.

D. [N,N'-Bis(2,3-dihydroxypropyl)]-5-[[dihydro-5-(hydroxymethyl)-2(3H)-furanylidene]amino]-2,4,6-triiodo-1,3-benzenedicarboxamide A solution of the title C compound (22.3 g, 22 mmol) in methanol (150 mL) was treated with sodium methoxide (23 mmol) in methanol (16 mL) and the mixture was stirred at room temperature for 3 hours. At the end of this time, the pH of the solution was adjusted to 6 with the ion exchange resin Dowex-50(H)$^+$. The resin was filtered off, the methanol removed in vacuo and the residue, thus obtained, dissolved in water (150 mL) and then treated three times with decolorizing charcoal (3×1 g), filtered and the solvent removed to obtain the crude product as a beige glassy solid (17.50 g). HPLC analysis showed the purity of this material to be 97.7%. This product (17.50 g) was further purified by reverse phase column chromatography, using the nonionic CHP-20 resin using aqueous ethanol as eluent. The desired product was obtained as a colorless glassy solid (15.95 g). 1.00 g of this material was crystallized from hot butanol (30 mL) to afford the title compound (970 mg) as colorless needles. TLC: $R_f$ 0.3 in ethyl acetate/methanol (7:3). Mass Spectrum: m/z (M+H)$^+$ 804, 713, 587.

Elemental analysis calc'd for $C_{19}H_{24}I_3N_3O_3 \cdot 0.85 H_2O$: C, 27.88; H, 3.16; I, 46.52; N, 5.14; O, 15.64; Found: C, 28.03; H, 2.99; I, 46.35; N, 4.92; $H_2O$, 1.87.

EXAMPLE 2

5-[[Dihydro-5-(hydroxymethyl)-2(3H)-furanylidene]-amino]-N,N'-bis[(2-hydroxy)-1-(hydroxymethyl)ethyl]-2,4,6-triiodo-1,3-benzenedicarboxamide A. N,N'-Bis[2-(acetyloxy)-1-[(acetyloxy)-methyl]ethyl]-2,4,6-triiodo-5-[(1-oxo-4-pentenyl)amino]-1,3-benzenedicarboxamide 4-Pentenoyl chloride (11.9 g, 100 mmol) was added to a stirred solution of N,N'-bis-[2-(acetyloxy)-1-[(acetyloxy)-methyl]ethyl]-5-amino-2,4,6-triiodo-1,3-benzenedicarboxamide (47.75 g, 50 mmol) in dimethylacetamide (400 mL) at room temperature and the mixture was stirred for 16 hours. Dimethylacetamide was removed in vacuo and the residue dissolved in ethyl acetate (600 ml). The solution was washed with aqueous sodium bicarbonate (10%, 2×150 mL) and with water (2×100 mL) and brine (150 mL). The organic layer was dried and the solvent removed to obtain the crude product as an off-white solid. Further purification by crystallization from a mixture of acetone (250 mL) and hexane (75 mL) afforded the title A compound (42.5 g), m.p. 162°–64°. TLC: $R_f$ 0.55 in ethyl acetate. Mass Spectrum: m/z 956 (M+H)$^+$, 830, 653.

Elemental Analysis calc'd for $C_{27}H_{32}I_3N_3O_{11}$: C, 33.95; H, 3.38; N, 4.40; I, 39.85; Found: C, 33.93; H, 3.18; N, 4.22; I, 39.84.

B. N,N'-Bis[2-(acetyloxy)-1-[(acetyloxy)-methyl]ethyl]-5-[[dihydro-5-(iodomethyl)-2(3H)-furanylidene]amino]-2,4,6-triiodo-1,3-benzenedicarboxamide To a solution of the title A compound (9.55 g, 10 mmol) in chloroform (200 mL), N-iodosuccinimide (4.48 g, 20 mmol) was added and the mixture heated at 50° for 1 hour. The progress of this reaction was monitored both by TLC and by reverse phase HPLC. At the end of 1 hour, the reaction was found to be complete. Chloroform was distilled off, the residue thus obtained dissolved in ethyl acetate (200 mL) and the resulting solution washed successively with water (100 mL), aqueous sodium thiosulfate (25%, 2×50 mL), and water (2×100 mL). The organic layer was dried and the solvent removed to obtain the product as a light yellow glassy solid (10.2 g). This crude product was further purified by column chromatography over silica gel (200 g) using a mixture of ethyl acetate and hexane (7:3) as eluent to obtain the title B compound as a glassy solid (8.5 g), m.p. 126°–30° (froaths), 145°–50° (decomposes).

Elemental analysis calc'd for $C_{27}H_{31}I_4N_3O_{11}$: C, 29.99; H, 2.91; N, 3.89; I, 46.95; Found: C, 30.04; H, 2.81; N, 3.77; I, 47.05.

C. N,N'-Bis[2-(acetyloxy)-1-[(acetyloxy)methyl]-ethyl]-5-[[5-[acetyloxy)methyl]dihydro-2-(3H)-furanylidene]amino]-2,4,6-triiodo-1,3-benzenedicarboxamide To a solution of the title B compound (7.5 g, 6.93 mmol) in glacial acetic acid (100 mL), was added silver acetate (3.34 g, 20 mmol), and the mixture stirred at 80° for 16 hours. The insoluble materials were filtered off, acetic acid removed in vacuo at 60°, the residue dissolved in ethyl acetate (250 mL), and the resulting solution washed successively with water (100 mL), aqueous sodium bicarbonate (100 mL) and water (100 mL). The ethyl acetate layer was dried and removal of the solvent afforded the crude product as a red colored solid. The crude material was chromatographed over silica gel (200 g, 250 cm column length) eluting with a solvent gradient varying from 25% hexane in ethyl acetate to 10% hexane in ethyl acetate to obtain the title C compound as a pink glassy solid (5.5 g), m.p. 172°–75°.

Elemental analysis calc'd for $C_{29}H_{34}I_3N_3O_{13}$: C, 34.37; H, 3.38; N, 4.15; I, 37.57; Found: C, 34.22; H, 3.50; N, 4.06; I, 37.82.

D. 5-[[Dihydro-5-(hydroxymethyl)-2(3H)-furanyl-idene]amino]-N,N'-bis[(2-hydroxy)-1-(hydroxy-methyl)ethyl]-2,4,6-triiodo-1,3-benzene-dicarboxamide A solution of the title C compound (2.7 g, 2.66 mmol) in methanol (50 mL) was treated with sodium methoxide (2.6 mmol) in methanol (6 mL) and the mixture was stirred at room temperature for 3 hours. At the end of this time, the pH of the solution was adjusted to 6 with the ion exchange resin Dowex-50-(H)$^+$. The resin was filtered off, the methanol removed in vacuo and the residue, thus obtained, dissolved in water (150 ml) and then treated three times with decolorizing charcoal (0.3 g), filtered and the solvent removed to obtain a beige glassy solid (2.1 g). This product was further purified by reverse phase column chromatography, using the nonionic CHP-20 resin and aqueous ethanol as eluant to obtain the pure title compound (1.85 g), m.p. 208°–10° (softens), 258°–62° (froths), 285°–89° (decomposes).

Elemental analysis calc'd for $C_{19}H_{24}N_3I_3O_8 \cdot 0.6 H_2O$: C, 28.04; H, 3.12; N, 5.16; I, 46.58; Found: C, 28.15; H, 3.28; N, 5.21; I, 46.78; $H_2O$, 1.32.

What is claimed is:

1. A compound of the formula

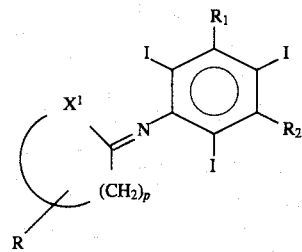

wherein R is selected from hydrogen, alkyl, hydroxy, alkoxy, hydroxyalkyl and alkoxyalkyl;

$X_1$ is

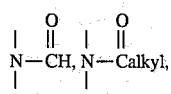

—S— or —O—;
p is 2–5;
$R_1$ is

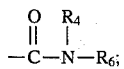

$R_2$ is

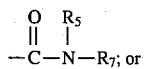

$R_2$ can also be —W—Z, where Z is

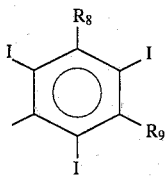

W is a linking group; and wherein
$R_8$ is

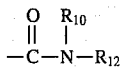

or heterocyclo;
$R_9$ is

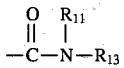

or heterocyclo;
$R_4$, $R_5$, $R_{10}$ and $R_{11}$ are the same or different and are hydrogen, alkyl or hydroxyalkyl;
$R_6$, $R_7$, $R_{12}$ and $R_{13}$ are the same or different and are hydrogen, alkyl and hydroxyalkyl;
W is —X—Y—X— wherein
X is

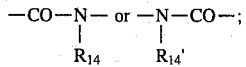

Y is

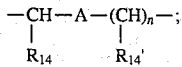

$R_{14}$ and $R_{14}'$ are independently H, alkyl or hydroxyalkyl;
A is a single bond, —O—, —S— or —N—$COR_{14}$;
n is 0 to 6.

2. The compound of claim 1 wherein
$X^1$ is oxygen;
p is 3;
R is hydroxyalkyl selected from

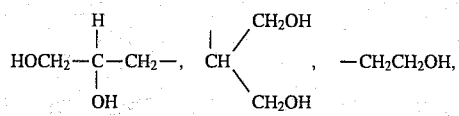

$R_4$ and $R_5$ are each hydrogen; and
$R_6$ and $R_7$ are each hydroxyalkyl.

3. The compounds of claim 1 wherein

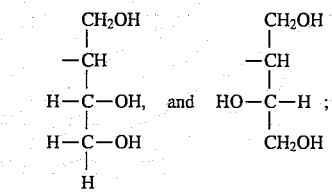

is $R_4$ and $R_5$ are each hydrogen; and,
$R_6$ and $R_7$ are each

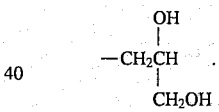

4. The compounds of claim 3 wherein $R_6$ and $R_7$ are each

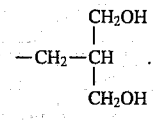

5. A compound of claim 1 having the name [N,N'-bis(2,3-dihydroxypropyl)-5- [[dihydro-5-(hydroxymethyl)-2(3H)-furanylidene]amino]-2,4,6-triiodo-1,3-benzenedicarboxamide.

6. A compound of claim 1 having the name 5-[[dihydro-5-(hydroxymethyl)-2(3H)-furanylidene]-amino] -N,N'-bis[(2-hydroxy)-1-(hydroxymethyl)ethyl]-2,4,6-triiodo-1,3-benzenedicarboxamide.

* * * * *